(12) United States Patent
Osborne, II

(10) Patent No.: US 7,457,506 B1
(45) Date of Patent: Nov. 25, 2008

(54) LINE ORGANIZER

(75) Inventor: Tommy T. Osborne, II, Cape Charles, VA (US)

(73) Assignee: Osborne Orthopedic Group, Inc., Nassawadox, VA (US)

( * ) Notice: Subject to any disclaimer, the term of this patent is extended or adjusted under 35 U.S.C. 154(b) by 102 days.

(21) Appl. No.: 11/323,880

(22) Filed: Dec. 30, 2005

(51) Int. Cl.
*G02B 6/46* (2006.01)
*F16L 3/22* (2006.01)

(52) U.S. Cl. ............ 385/136; 248/68.1; 248/74.1
(58) Field of Classification Search .......... 385/136; 248/62, 68.1, 67.7, 74.1–74.5
See application file for complete search history.

(56) References Cited

U.S. PATENT DOCUMENTS

| | | | |
|---|---|---|---|
| D263,624 S | 3/1982 | Stenzler et al. | |
| 4,705,244 A | 11/1987 | Saotome et al. | |
| 4,775,121 A * | 10/1988 | Carty | 248/68.1 |
| D298,355 S | 11/1988 | Young | |
| 4,971,271 A | 11/1990 | Sularz | |
| 4,988,062 A | 1/1991 | London | |
| 5,115,542 A * | 5/1992 | Gehres | 24/543 |
| 5,184,794 A * | 2/1993 | Saito | 248/68.1 |
| D378,408 S | 3/1997 | Pyeatt et al. | |
| 5,613,655 A * | 3/1997 | Marion | 248/68.1 |
| D379,509 S | 5/1997 | Macko | |
| 5,820,048 A * | 10/1998 | Shereyk et al. | 248/68.1 |
| 6,164,604 A * | 12/2000 | Cirino et al. | 248/74.3 |
| 6,345,873 B1 | 2/2002 | Kim | |
| D488,054 S | 4/2004 | Myers | |
| D503,231 S | 3/2005 | Daugherty | |
| 2002/0070317 A1* | 6/2002 | Goodman | 248/74.1 |
| 2003/0132352 A1 | 7/2003 | Weaver | |
| 2004/0118982 A1 | 6/2004 | Shillings et al. | |
| 2005/0006534 A1 | 1/2005 | Shillings | |

* cited by examiner

*Primary Examiner*—Michelle R Connelly Cushwa
(74) *Attorney, Agent, or Firm*—Bowman Green Hampton & Kelly, PLLC

(57) ABSTRACT

A line organizer, comprising an elongate lower portion, wherein the lower portion includes at least two lower aperture portions formed in the lower portion; a base member associated with the lower portion; an elongate upper portion, wherein the upper portion includes at least two upper aperture portions formed in the upper portion, wherein each upper aperture portion corresponds to a lower aperture portion, and wherein the upper portion is coupled to the lower portion via a hinge means, such that the upper portion and the lower portion are pivotable relative to one another and are pivotable between a closed position and an open position; and a locking means associated with the upper portion and the lower portion, wherein the locking means is capable of maintaining the upper and lower portions in the closed position.

15 Claims, 6 Drawing Sheets

LINE ORGANIZER

BACKGROUND OF THE INVENTION

1. Field of the Invention

This invention relates generally to line organizers. In particular, the present invention relates to a medical line organizer.

2. Description of Related Art

During certain surgical or other medical procedures, a number of devices, tools, or instruments are used to monitor the patient's body functions, supply medications and fluids to the patient's body, remove fluids from the patient's body, and/or perform the actual procedure. Generally, this means that a large number of wires, cables, hoses, tubes, or other lines are placed around and often over the patient.

When a large number of lines are present, the lines can become entangled and individual lines can become difficult to identify, particularly in emergency situations. Additionally, lines may be inadvertently pulled or tugged, which could result in stress to the patient's body at the attachment or entry site of the line or the line being disconnected from the patient or the attached device.

SUMMARY OF THE INVENTION

The present invention relates generally to line organizers. In particular, the present invention relates to a medical line organizer that allows a plurality of wires, cables, hoses, tubes, or other lines to be arranged and maintained in an organized fashion.

In various illustrative, non-limiting embodiments of this invention, the line organizer includes an elongate upper and lower portion that are pivotably coupled proximate one end. The lower portion includes an associated base member that provides a level of stability to the line organizer.

The upper and/or lower portions include a plurality of corresponding aperture portions, such that when the upper portion and the lower portion are in a closed position relative to one another, individual wires, cables, hoses, tubes, or other lines can be captured within the apertures formed by corresponding aperture portions.

When the lines are captured in the apertures, a locking means may be employed to maintain the upper and lower portions in the closed position.

In various exemplary, non-limiting, embodiments of this invention, the line organizer can also provide a measure of isolation for the various lines between the patient's body and the attached device, so that if the lines are inadvertently pulled or tugged, the line organizer will hold the line in place.

Accordingly, this invention provides a line organizer that is capable of receiving and holding a plurality of wires, cables, hoses, tubes, or other lines.

This invention separately provides a line organizer that is capable of keeping a plurality of wires, cables, hoses, tubes, or other lines from becoming entangled.

This invention separately provides a line organizer that is capable of maintaining a plurality of wires, cables, hoses, tubes, or other lines in an arranged and organized fashion.

This invention separately provides a line organizer that permits easy access to the captured lines.

This invention separately provides a line organizer that allows captured lines to be more easily identified.

This invention separately provides a line organizer, which is capable of being manufactured using injection molding production techniques.

These and other features and advantages of this invention are described in or are apparent from the following detailed description of the exemplary embodiments.

BRIEF DESCRIPTION OF THE DRAWINGS

The exemplary embodiments of this invention will be described in detail, with reference to the following figures, wherein like reference numerals refer to like parts throughout the several views, and wherein.

DETAILED DESCRIPTION OF EXEMPLARY EMBODIMENT(S)

For simplicity and clarification, the design factors and operating principles of the line organizer according to this invention are explained with reference to various exemplary, non-limiting embodiments of a line organizer according to this invention. The basic explanation of the design factors and operating principles of the line organizer is applicable for the understanding, design, and implementation of the line organizer of this invention.

It should also be appreciated that the terms "line" and "line organizer" are used for basic explanation and understanding of the operation of the systems, methods, and apparatuses of this invention. Therefore, the terms "line" and "line organizer" are not to be construed as limiting the systems, methods, and apparatuses of this invention.

It should also be understood that this invention is not limited to the particular exemplary embodiments set forth and may, of course, vary. Various changes may be made to the described line organizer and equivalents may be substituted without departing from the true spirit and scope of the invention. In addition, many modifications may be made to adapt a particular situation, material, composition of matter, process, process step, or steps, to the objective, spirit, and scope of the present invention. All such modifications are intended to be within the scope of the claims made herein. Furthermore, it is contemplated that any optional feature of the inventive variations described herein may be set forth and claimed independently, or in combination with any one or more of the features described herein.

Unless defined otherwise, all technical and scientific terms used herein have the same meaning as commonly understood by one of ordinary skill in the art to which this invention belongs. However, it should be appreciated that exemplary, non-limiting methods and materials are described herein and any methods and/or materials similar or equivalent to those described herein can be used in practicing the present invention.

In addition, it is noted that as used herein and in the appended claims, the singular forms "a", "and", "said", and "the" include plural referents unless the context clearly dictates otherwise. Conversely, it is contemplated that the claims may be so-drafted as to require singular elements or exclude any optional element indicated to be so in the text or drawings.

Figure 1:
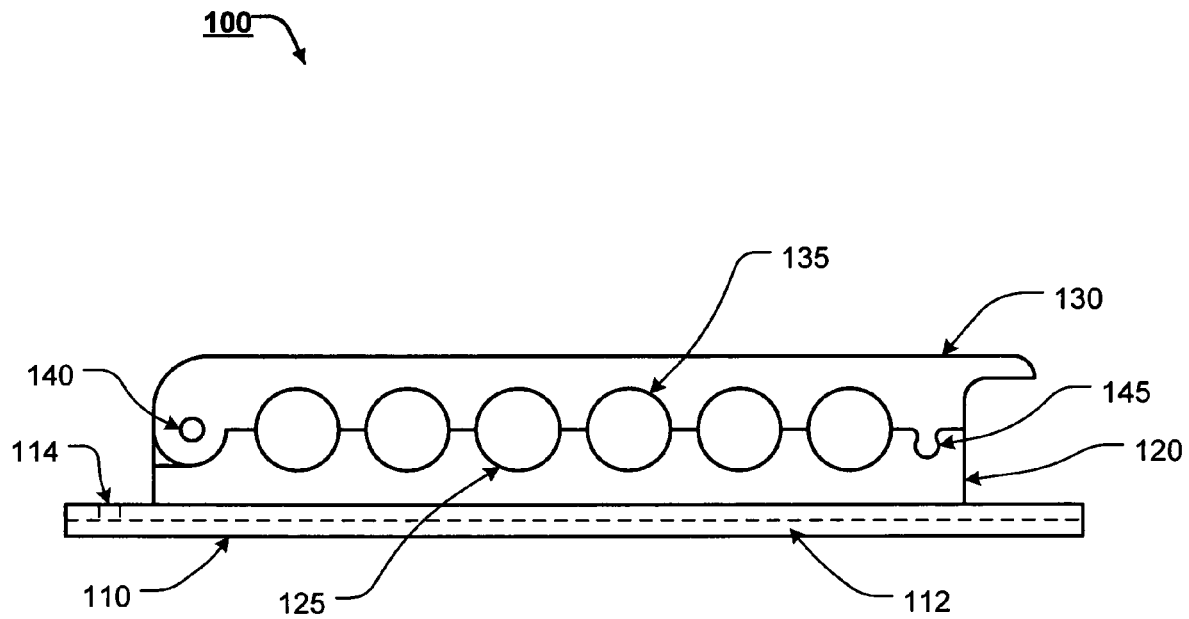
FIG. 1 shows a side view of a first exemplary embodiment of a line organizer according to this invention, wherein the line organizer is in a closed position.
Figure 2:
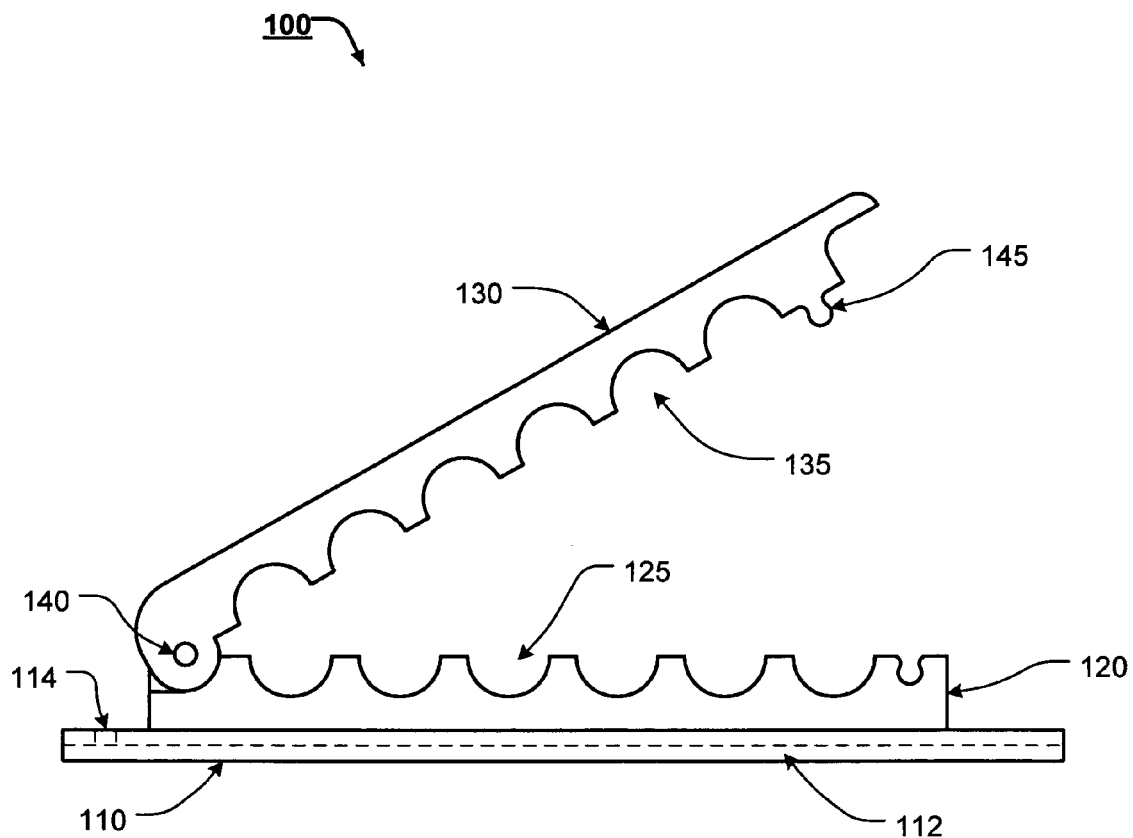
FIG. 2 shows a side view of the first exemplary embodiment of a line organizer according to this invention, wherein the line organizer is in an opened position.
Figure 3:
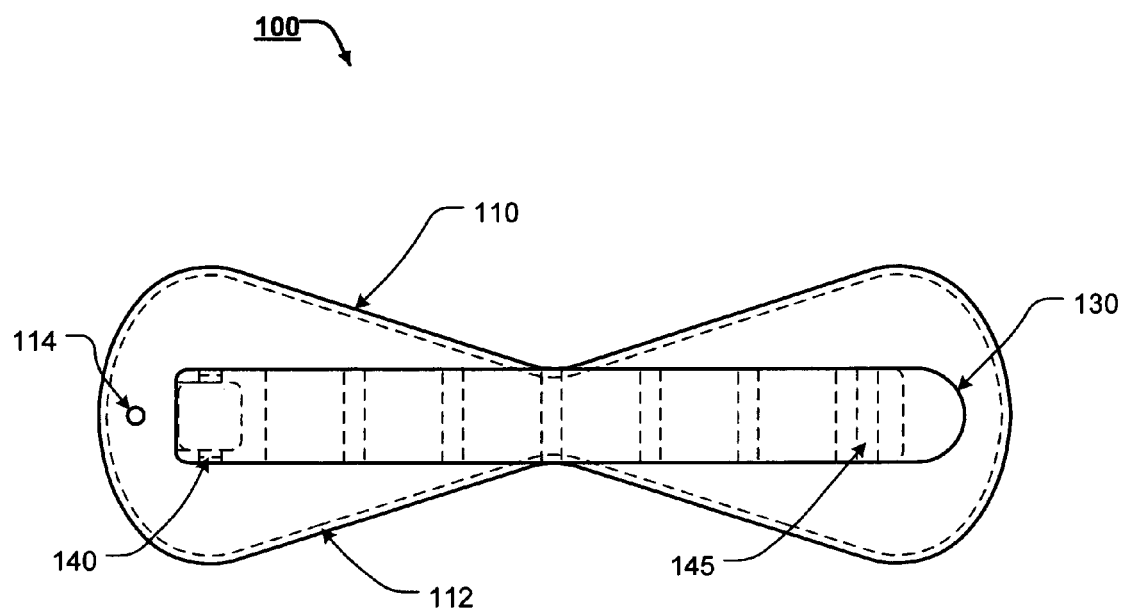
FIG. 3 shows a top view of the first exemplary embodiment of a line organizer according to this invention.
Figure 4:
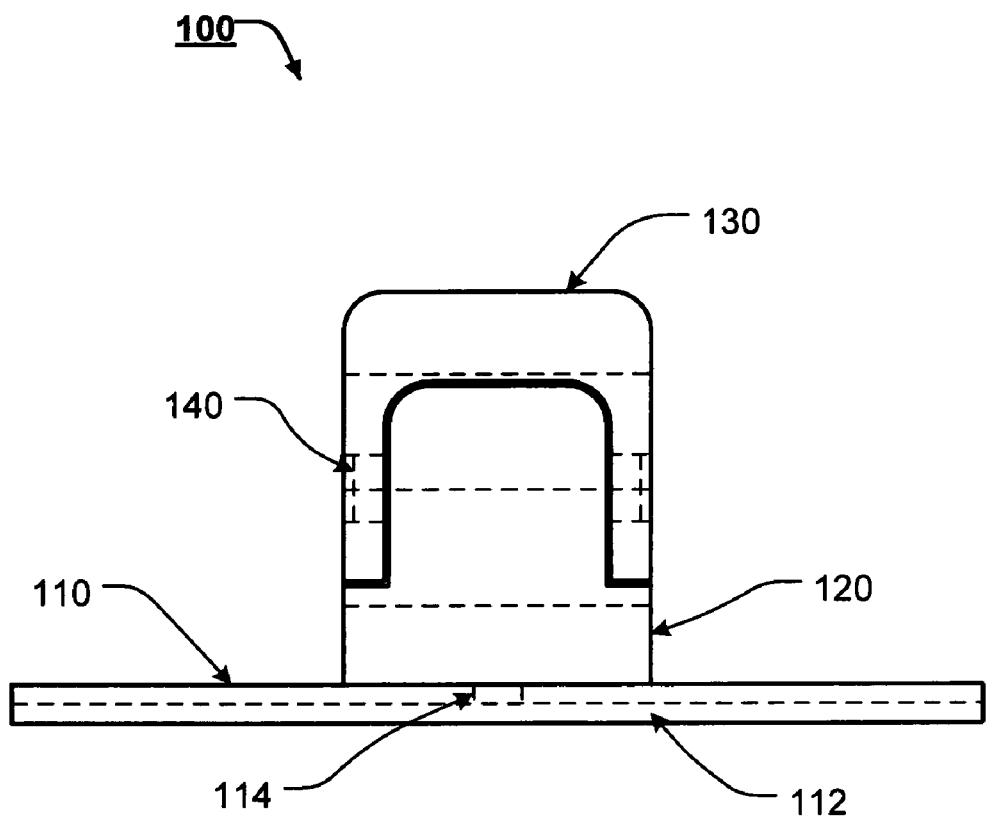
FIG. 4 shows an end view of the first exemplary embodiment of a line organizer according to this invention.

Turning now to FIGS. 1-4, FIGS. 1 and 2 show a side view of a first exemplary embodiment of a line organizer according to this invention. FIG. 1 shows the line organizer 100 in a closed position, while FIG. 2 shows the line organizer 100 in an open position. FIG. 3 shows a top view of the line organizer 100, while FIG. 4 shows an end view of the line organizer 100. As illustrated in FIGS. 1-4, the line organizer 100 comprises at least some of a base member 110, a lower portion 120, an upper portion 130, a hinge means 140, and a locking means 145.

The lower portion 120 and the upper portion 130 each comprise a substantially elongate portion of material. One or more lower aperture portions 125 is formed in the lower portion 120, while one or more corresponding upper aperture portions 135 is formed in the upper portion 130.

The lower portion 120 and the upper portion 130 are pivotably coupled, via the hinge means 140, such that the upper portion 130 and the lower portion 120 are pivotable relative to one another and are pivotable between a closed position, as illustrated in FIG. 1, and an opened position, as illustrated in FIG. 2.

In various exemplary embodiments, the hinge means 140 comprises a pivot pin that extends all or a portion of the way across a width of the lower portion 120 and the upper portion 130. In other exemplary embodiments, the hinge means 140 comprises a portion of a material that flexibly couples the lower portion 120 to the upper portion 130.

In various exemplary embodiments, the lower portion 120 and the upper portion 130 are biased to the open position.

When the upper portion 130 and the lower portion 120 are in a closed position, each corresponding upper aperture portion 135 and lower aperture portion 125 is aligned so as to form a line capturing aperture.

The lower portion 120 further includes an associated base member 110. In various exemplary embodiments, the base member 110 is formed as an integral part of the lower portion 120. Alternatively, the base member 110 may be permanently or removably coupled to the lower portion 120. The base member 110 extends from the lower portion 120 and provides a level of stability to the line organizer 100. As shown in FIG. 3, the base member 110 comprises a substantially hourglass shape. However, it should be appreciated that the overall size and shape of the base member 100 is a design choice based on the desired appearance and functionality of the line organizer 100.

In various exemplary embodiments, the base member 100 includes a rim or lip 112, which extends substantially downwardly from an outer edge of the base member 100.

In various exemplary embodiments, the base member 100 includes a hole or aperture 114 formed through the base member 100. If included, the aperture 114 provides a means for the base member 100 to be attached or coupled to a specific surface and/or device.

In various exemplary embodiments, the base member 100 may comprise an attachment or coupling means (not shown) that allows the line organizer 100 to be attached or coupled to a specific surface and/or device. In various exemplary embodiments, the coupling means may comprise a hook and loop fastener, such as Velcro or other attachment means or releasable fasteners, such as, for example, a male/female snap-release buckle, a ziplock fastening device, a zipper, pin, button, snap, clamp, or any other known or later developed attachment or coupling means.

The upper and/or lower portions include a plurality of corresponding aperture portions, such that when the upper portion and the lower portion are in a closed position relative to one another, individual wires, cables, hoses, tubes, or other lines can be captured within the apertures formed by corresponding aperture portions.

When the upper portion 130 and the lower portion 120 are in a closed position, a locking means 145 may be employed to maintain the upper and lower portions in the closed position. In various exemplary embodiments, the locking means 145 comprises a mating protrusion formed on, for example, the upper portion 130 and a recess formed in, for example, the lower portion 120.

In various exemplary embodiments, various portions of the line organizer 100 are formed of a plastic or polymeric material, such as a polymeric composite. Alternate materials of construction may include one or more of the following: wood, steel, aluminum, titanium, and/or other metals, as well as various alloys and composites thereof, glass-hardened polymers, polymer or fiber reinforced metals, carbon fiber or glass fiber composites, continuous fibers in combination with thermoset and thermoplastic resins, chopped glass or carbon fibers used for injection molding compounds, laminate glass or carbon fiber, epoxy laminates, woven glass fiber laminates, impregnate fibers, polyester resins, epoxy resins, phenolic resins, polyimide resins, cyanate resins, high-strength plastics, nylon, glass or polymer fiber reinforced plastics, thermoform and/or thermoset sheet materials, and/or various combinations of the foregoing. Thus, it should be understood that the material or materials used to form the various portions of the line organizer 100 is a design choice based on the desired appearance and functionality of the line organizer 100.

During use of the line organizer 100, any locking means 145 is undone for overcome and the upper portion 130 is pivoted, via the hinge means 140, such that the line organizer 100 is presented in the opened position. Lines are then arranged in the lower aperture portions 125, as desired.

When all of the desired lines have been arranged in the lower aperture portions 125, the upper portion 130 is pivoted, via the hinge means 140, so that the line organizer 100 is in the closed position. As the upper portion 130 is moved to the closed position, the upper aperture portions 135 mate with the corresponding lower aperture portions 125 to form line apertures that capture the lines of arranged in the lower aperture portions 125.

When the lines are captured in the apertures, the locking means 145 may be employed to maintain the line organizer 100 in the closed position.

It should be appreciated that the number, size, shape, and placement of any included upper aperture portions 135 and lower aperture portions 125 is a design choice based on the particular line that may be held by or within the upper aperture portions 135 and the lower aperture portions 125. Thus, it should be understood that the elements of the line organizer 100 may be scaled based on the desired functionality of the line organizer 100.

Figure 5:
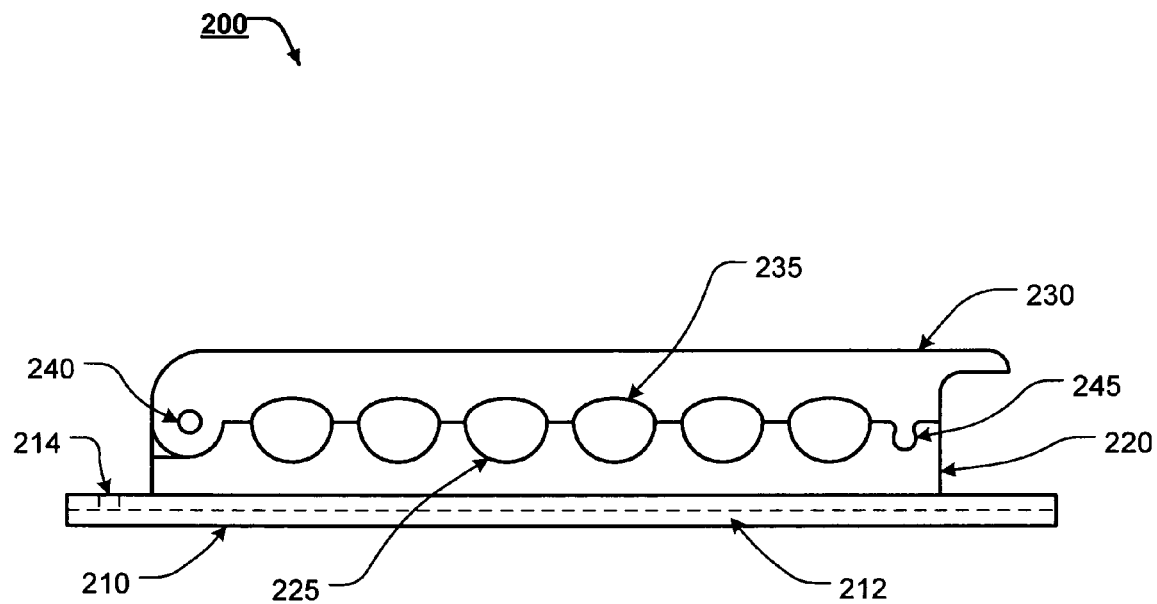
FIG. 5 shows a side view of a second exemplary embodiment of a line organizer according to this invention, wherein the line organizer is in a closed position.

FIG. 5 shows a side view of a second exemplary embodiment of a line organizer according to this invention. As shown in FIG. 5, the line organizer 200 comprises at least some of a base member 210, a lip 212, an aperture 214, a lower portion 220, an upper portion 230, a hinge means 240, and a locking means 245. One or more lower aperture portions 225 is formed in the lower portion 220, while one or more corresponding upper aperture portions 235 is formed in the upper portion 230.

It should be understood that each of these elements corresponds to and operates similarly to the base member 110, the lip 112, the aperture 114, the lower portion 120, the lower aperture portions 125, the upper portion 130, the upper aperture portions 135, the hinge means 140, and the locking means 145, as described above with reference to the line organizer 100 of FIGS. 1-4.

However, as shown in FIG. 5, the shape of the lower aperture portions 225 differs from the shape of the upper aperture portions 235. Furthermore, the line organizer 200 is shown as including both large and small aperture portions.

Figure 6:
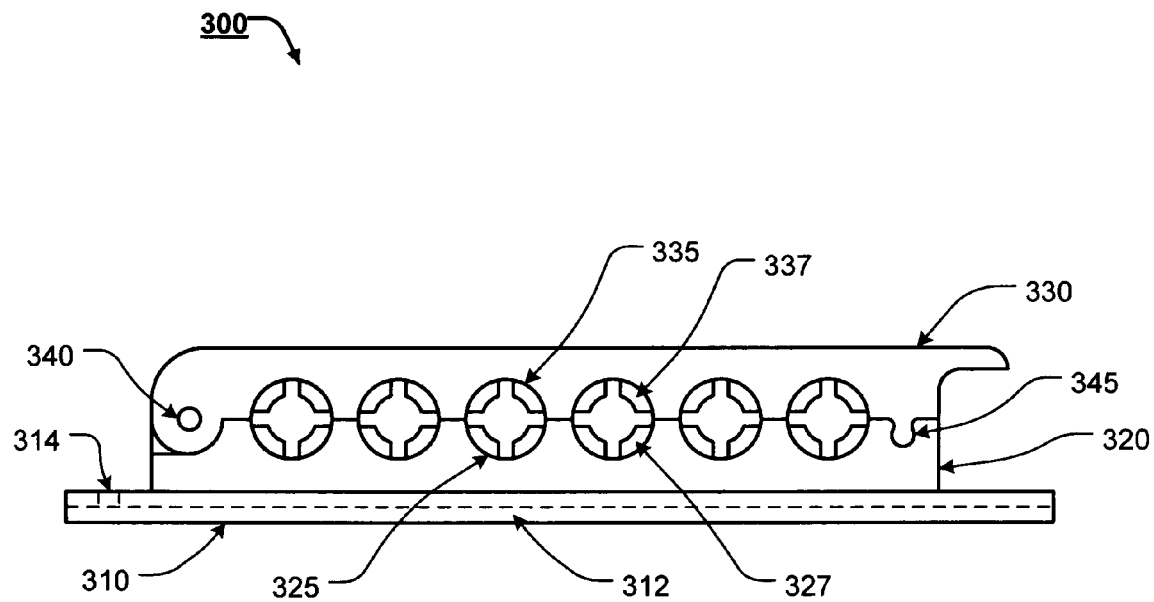
FIG. 6 shows a side view of a third exemplary embodiment of a line organizer according to this invention, wherein the line organizer is in a closed position.

FIG. 6 shows a side view of a third exemplary embodiment of a line organizer according to this invention. As shown in FIG. 6, the line organizer 300 comprises at least some of a base member 310, a lip 312, an aperture 314, a lower portion 320, an upper portion 330, a hinge means 340, and a locking means 345. One or more lower aperture portions 325 is formed in the lower portion 320, while one or more corresponding upper aperture portions 335 is formed in the upper portion 330.

It should be understood that each of these elements corresponds to and operates similarly to the base members 110 and 210, the lip 112 and 212, the aperture 114 and 214, the lower portions 120 and 220, the lower aperture portions 125 and 225, the upper portions 130 and 230, the upper aperture portions 135 and 235, the hinge means 140 and 240, and the locking means 145 and 245, as described above with reference to the line organizers 100 and 200 of FIGS. 1-5.

However, as shown in FIG. 6, flexible extensions 327 are positioned around a portion of the inner wall of the lower aperture portions 325. Likewise, flexible extensions 337 are positioned around a portion of the inner wall of the upper aperture portions 335. The flexible extensions allow the lower aperture portions 325 and the upper aperture portions 335 to more securely capture any lines placed with the aperture portions.

It should be appreciated that, in various exemplary embodiments, the flexible extensions comprise a flexible and/or collapsible material, such as, for example, rubber or silicon, which flexes to accommodate and hold a variety of line diameters.

While this invention has been described in conjunction with the exemplary embodiments outlined above, it is evident that many alternatives, modifications, and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A line organizer, comprising:
    an elongate lower portion, wherein the lower portion includes at least two lower aperture portions formed in the lower portion;
    a base member formed as an integral part of the lower portion, wherein at least a portion of the base member extends beyond a width of the lower portion;
    an elongate upper portion, wherein the upper portion includes at least two upper aperture portions formed in the upper portion, wherein each upper aperture portion corresponds to a lower aperture portion, and wherein the upper portion is coupled to the lower portion via a hinge means, such that the upper portion and the lower portion are pivotable relative to one another and are pivotable between a closed position and an open position; and
    a locking means associated with the upper portion and the lower portion, wherein the locking means is capable of maintaining the upper and lower portions in the closed position.

2. The line organizer of claim 1, wherein the upper portion and the lower portion are in a closed position, each corresponding upper aperture portion and lower aperture portion is substantially aligned so as to form a line capturing aperture.

3. The line organizer of claim 1, wherein a shape of at least one lower aperture portion differs from a shape of at least one upper aperture portion.

4. The line organizer of claim 1, wherein a flexible extension is positioned around a portion of an inner wall of at least one lower aperture portion and a flexible extension is positioned around a portion of an inner wall of at least one upper aperture portion.

5. The line organizer of claim 1, wherein the hinge means comprises a pivot pin that extends at least a portion part of the way across a width of the lower portion and the upper portion.

6. The line organizer of claim 1, wherein the hinge means comprises a portion of a material that flexibly couples the lower portion to the upper portion.

7. The line organizer of claim 1, wherein the upper portion and the lower portion are biased to the open position.

8. The line organizer of claim 1, wherein the base member is formed as an integral part of the lower portion.

9. The line organizer of claim 1, wherein the base member is permanently coupled to the lower portion.

10. The line organizer of claim 1, wherein the base member is removably coupled to the lower portion.

11. The line organizer of claim 1, wherein the base member comprises a substantially hourglass shape.

12. The line organizer of claim 1, wherein the base member comprises a coupling means that allows the line organizer to be attached or coupled to a specific surface and/or device.

13. The line organizer of claim 1, wherein the locking means comprises a mating protrusion formed on the upper portion and a recess formed in the lower portion.

14. A line organizer, comprising:
    an elongate lower portion, wherein the lower portion includes a plurality of lower aperture portions formed in the lower portion;
    a base member formed as an integral part of the lower portion, wherein at least a portion of the base member extends beyond a width of the lower portion;
    an elongate upper portion, wherein the upper portion includes a plurality of upper aperture portions formed in the upper portion, wherein each upper aperture portion corresponds to a lower aperture portion;
    a hinge means, wherein the hinge means pivotably couples the upper portion to the lower portion, such that the upper portion and the lower portion are pivotable between a closed position and an open position; and
    a locking means associated with the upper portion and the lower portion, wherein the locking means is capable of maintaining the upper and lower portions in the closed position.

15. A method for using a line organizer, the line organizer comprising:
    an elongate lower portion, wherein the lower portion includes a plurality of lower aperture portions formed in the lower portion;
    a base member formed as an integral part of the lower portion, wherein at least a portion of the base member extends beyond a width of the lower portion;

an elongate upper portion, wherein the upper portion includes a plurality of upper aperture portions formed in the upper portion, wherein each upper aperture portion corresponds to a lower aperture portion;

a hinge means, wherein the hinge means pivotably couples the upper portion to the lower portion, such that the upper portion and the lower portion are pivotable between a closed position and an open position;

a locking means associated with the upper portion and the lower portion, wherein the locking means is capable of maintaining the upper and lower portions in the closed position;

the method comprising;

providing the line organizer in an open position;

arranging at least one line in at least one lower aperture portion;

pivoting the upper portion, so that the upper aperture portions mate with corresponding lower aperture portions to form line apertures and capture the at least one line arranged in the lower aperture portion, such that the line organizer is in a closed position;

locking, via the locking means, the line organizer in the closed position.

* * * * *